(12) United States Patent
Raman et al.

(10) Patent No.: US 7,381,182 B2
(45) Date of Patent: *Jun. 3, 2008

(54) METHOD AND APPARATUS FOR EXTERNAL HEART STABILIZATION

(75) Inventors: JaiShanker Raman, Chicago, IL (US); P. Srirama Rao, San Diego, CA (US)

(73) Assignee: Mardil, Inc., Morrisville, NC (US)

(*) Notice: Subject to any disclaimer, the term of this patent is extended or adjusted under 35 U.S.C. 154(b) by 780 days.

This patent is subject to a terminal disclaimer.

(21) Appl. No.: 10/796,580

(22) Filed: Mar. 8, 2004

(65) Prior Publication Data

US 2004/0267329 A1   Dec. 30, 2004

Related U.S. Application Data

(63) Continuation of application No. 10/236,640, filed on Sep. 6, 2002, now Pat. No. 6,716,158.

(60) Provisional application No. 60/318,172, filed on Sep. 7, 2001.

(51) Int. Cl.
*A61B 19/00*   (2006.01)
(52) U.S. Cl. ...................................... 600/37
(58) Field of Classification Search ................ 600/37, 600/16–18; 607/129
See application file for complete search history.

(56) References Cited

U.S. PATENT DOCUMENTS

| | | |
|---|---|---|
| 3,983,863 A | 10/1976 | Janke et al. |
| 4,048,990 A | 9/1977 | Goetz |
| 4,403,604 A | 9/1983 | Wilkinson et al. |
| 4,428,375 A | 1/1984 | Ellman |
| 4,630,597 A | 12/1986 | Kantrowitz et al. |
| 4,690,134 A | 9/1987 | Snyders |
| 4,821,723 A | 4/1989 | Baker, Jr. et al. |
| 4,878,890 A | 11/1989 | Bilweis |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |

(Continued)

FOREIGN PATENT DOCUMENTS

WO   WO 98/14136   4/1998

(Continued)

OTHER PUBLICATIONS

Bolling et al., J. Thorac. Cardiovasc. Surg. (1998) 115:381-388.

(Continued)

*Primary Examiner*—John P Lacyk
(74) *Attorney, Agent, or Firm*—Gordon & Rees LLP

(57) ABSTRACT

The present disclosure is directed to an external cardiac basal annuloplasty system (ECBAS or BACE-System: basal annuloplasty of the cardia externally) and methods for treatment of regurgitation of mitral and tricuspid valves. The BACE-System provides the ability to correct leakage of regurgitation of the valves with or without the use of cardiopulmonary bypass, particularly when the condition is related to dilation of the base of the heart. This ECBAS invention can be applied to the base of the heart epicardially, either to prevent further dilation or to actively reduce the size of the base of the heart.

10 Claims, 7 Drawing Sheets

Cross Section of the Heart

U.S. PATENT DOCUMENTS

| | | |
|---|---|---|
| 5,057,117 A | 10/1991 | Atweh |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,192,314 A | 3/1993 | Daskalakis |
| 5,256,132 A | 10/1993 | Snyders |
| 5,290,217 A | 3/1994 | Campos |
| 5,356,432 A | 10/1994 | Rutkow et al. |
| 5,383,840 A | 1/1995 | Heilman et al. |
| 5,385,156 A | 1/1995 | Oliva |
| 5,429,584 A | 7/1995 | Chiu |
| 5,507,779 A | 4/1996 | Altman |
| 5,524,633 A | 6/1996 | Heaven et al. |
| 5,603,337 A | 2/1997 | Jarvik |
| 5,647,380 A | 7/1997 | Campbell et al. |
| 5,702,343 A | 12/1997 | Alferness |
| 5,713,954 A | 2/1998 | Rosenberg et al. |
| 5,800,528 A | 9/1998 | Lederman et al. |
| 5,961,440 A | 10/1999 | Schweich, Jr. et al. |
| 5,976,551 A | 11/1999 | Mottez et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,077,218 A | 6/2000 | Alferness |
| 6,085,754 A | 7/2000 | Alferness et al. |
| 6,123,662 A | 9/2000 | Alferness et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,646 B1 | 2/2001 | Kulisz et al. |
| 6,206,820 B1 | 3/2001 | Kazi |
| 6,221,103 B1 | 4/2001 | Melvin |
| 6,230,714 B1 | 5/2001 | Alferness et al. |
| 6,241,654 B1 | 6/2001 | Alferness |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,370,429 B1 | 4/2002 | Alferness et al. |
| 6,375,608 B1 | 4/2002 | Alferness |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,482,146 B1 | 11/2002 | Alferness et al. |
| 6,488,618 B1 | 12/2002 | Paolitto et al. |
| 6,494,825 B1 | 12/2002 | Talpade |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,544,168 B2 | 4/2003 | Alferness |
| 6,547,716 B1 | 4/2003 | Milbocker |
| 6,558,319 B1 | 5/2003 | Aboul-Hosn et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi et al. |
| 6,589,160 B2 | 7/2003 | Schweich, Jr. et al. |
| 6,592,514 B2 | 7/2003 | Kolata et al. |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,622,730 B2 | 9/2003 | Ekvall et al. |
| 6,629,921 B1 | 10/2003 | Schweich, Jr. et al. |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,627 B2 | 2/2004 | Jayaraman |
| 6,689,048 B2 | 2/2004 | Vanden Hoek et al. |
| 6,695,768 B1 | 2/2004 | Levine et al. |
| 6,695,769 B2 | 2/2004 | French et al. |
| 6,701,929 B2 | 3/2004 | Hussein |
| 6,702,732 B1 | 3/2004 | Lau et al. |
| 6,709,382 B1 | 3/2004 | Horner |
| 6,723,038 B1 | 4/2004 | Schroeder et al. |
| 6,723,041 B2 | 4/2004 | Lau et al. |
| 6,730,016 B1 | 5/2004 | Cox et al. |
| 6,746,471 B2 | 6/2004 | Mortier et al. |
| 6,755,777 B2 | 6/2004 | Schweich, Jr. et al. |
| 6,755,779 B2 | 6/2004 | Vanden Hoek et al. |
| 6,764,510 B2 | 7/2004 | Vidlund et al. |
| 6,776,754 B1 | 8/2004 | Wilk |
| 6,793,618 B2 | 9/2004 | Schweich, Jr. et al. |
| 6,808,488 B2 | 10/2004 | Mortier et al. |
| 6,852,076 B2 | 2/2005 | Nikolic et al. |
| 6,876,887 B2 | 4/2005 | Okuzumi et al. |
| 6,881,185 B2 | 4/2005 | Vanden Hock et al. |
| 2001/0016675 A1 | 8/2001 | Mortier et al. |
| 2001/0025171 A1 | 9/2001 | Mortier et al. |
| 2002/0029080 A1 | 3/2002 | Mortier et al. |
| 2002/0058855 A1 | 5/2002 | Schweich, Jr. et al. |
| 2002/0068849 A1 | 6/2002 | Schweich, Jr. et al. |
| 2002/0068850 A1 | 6/2002 | Vanden Hoek et al. |
| 2002/0077524 A1 | 6/2002 | Schweich, Jr. et al. |
| 2002/0147406 A1 | 10/2002 | Von Segesser |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0173694 A1 | 11/2002 | Mortier et al. |
| 2003/0032979 A1 | 2/2003 | Mortier et al. |
| 2003/0050529 A1 | 3/2003 | Vidlund et al. |
| 2003/0065248 A1 | 4/2003 | Lau et al. |
| 2003/0088149 A1 | 5/2003 | JaiShankar et al. |
| 2003/0130731 A1 | 7/2003 | Vidlund et al. |
| 2003/0166992 A1 | 9/2003 | Schweich, Jr. et al. |
| 2003/0171641 A1 | 9/2003 | Schweich, Jr. et al. |
| 2003/0181928 A1 | 9/2003 | Vidlund et al. |
| 2003/0233023 A1 | 12/2003 | Khaghani et al. |
| 2004/0002626 A1 | 1/2004 | Feld et al. |
| 2004/0034272 A1 | 2/2004 | Cesar et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0147805 A1 | 7/2004 | Lau et al. |
| 2004/0167374 A1 | 8/2004 | Schweich, Jr. et al. |
| 2004/0181124 A1 | 9/2004 | Alferness |

| | | |
|---|---|---|
| 2004/0186342 A1 | 9/2004 | Vanden Hock et al. |
| 2004/0210104 A1 | 10/2004 | Lau et al. |
| 2004/0225304 A1 | 11/2004 | Vidlund et al. |
| 2004/0243229 A1 | 12/2004 | Vidlund et al. |
| 2004/0249242 A1 | 12/2004 | Lau et al. |
| 2004/0267083 A1 | 12/2004 | McCarthy et al. |
| 2005/0004428 A1 | 1/2005 | Cox et al. |
| 2005/0010079 A1 | 1/2005 | Bertolero et al. |
| 2005/0014992 A1 | 1/2005 | Lau et al. |
| 2005/0020874 A1 | 1/2005 | Lau et al. |
| 2005/0054892 A1 | 3/2005 | Lau et al. |
| 2005/0059854 A1 | 3/2005 | Hoek et al. |
| 2005/0065396 A1 | 3/2005 | Mortier et al. |
| 2005/0075723 A1 | 4/2005 | Schroeder et al. |
| 2005/0085688 A1 | 4/2005 | Girard et al. |
| 2005/0090707 A1 | 4/2005 | Lau et al. |
| 2006/0063970 A1* | 3/2006 | Raman et al. ............. 600/37 |
| 2007/0129598 A1* | 6/2007 | Raman et al. ............. 600/37 |

FOREIGN PATENT DOCUMENTS

| | | |
|---|---|---|
| WO | WO9952470 A1 | 10/1999 |
| WO | WO9952471 | 10/1999 |
| WO | WO 00/28912 | 5/2000 |
| WO | WO 00/28918 | 5/2000 |
| WO | WO 01/03608 | 1/2001 |
| WO | WO0110421 A1 | 2/2001 |
| WO | WO 01/91667 | 12/2001 |
| WO | WO 01/95830 | 12/2001 |
| WO | WO 02/13726 | 2/2002 |
| WO | WO 02/00099 | 9/2002 |
| WO | WO0322131 A2 | 3/2003 |

OTHER PUBLICATIONS

Lamas et al., Circulation (1997) 96:827.
Liel-Cohen et al., Circulation (2000) 101(23):2756-2763.
Pai et al., Circulation (2000) 102(18)Suppl.II:369.
Timek et al., Circulation (2000) 102(18)Suppl.:420.
Bourge, "Clinical Trial Begins for Innovative Device-Altering Left Ventricular Shape in Heart Failure", UAB Insight, Aug. 8, 2002.

* cited by examiner

Cross Section of the Heart

Cross-Section of the Base of the Heart

Schematic Diagram of the Base of the Heart

Traditional method of repairing mitral and tricuspid valves with annuloplasty bands from inside the heart Basal Annuloplasty of the Cardia Externally

Fig. 6 BACE device

METHOD AND APPARATUS FOR EXTERNAL HEART STABILIZATION

This application claims priority under 35 U.S.C. §120 as a continuation of U.S. patent application Ser. No. 10/236,640 filed Sep. 6, 2002, now U.S. Pat. No. 6,716,158, which application claims priority under 35 U.S.C. 119(e) to provisional application 60/318,172 filed 07 Sep. 2001,the contents of which are incorporated herein by reference.

FIELD OF THE INVENTION

The present invention relates to devices and methods for treating dilatation of the valves at the base of the heart by external stabilization of the base of the heart, which subtend the atrio-ventricular valves of the heart.

BACKGROUND OF THE ART

Dilatation of the base of the heart occurs with various diseases of the heart and often is a causative mechanism of heart failure. In some instances, depending on the cause, the dilatation may be localized to one portion of the base of the heart (e.g., mitral insufficiency as a consequence of a heart attack affecting the inferior and basal wall of the left ventricle of the heart), thereby affecting the valve in that region. In other cases, such as cardiomyopathy, the condition may be global affecting more of the heart and its base, causing leakage of particularly the mitral and tricuspid valves. Other conditions exist where the mitral valve structure is abnormal, predisposing to leakage and progressive dilatation of the valve annulus (area of valve attachment to the heart). This reduces the amount of blood being pumped out by the ventricles of the heart, thereby impairing cardiac function further.

In patients with heart failure and severe mitral insufficiency, good results have been achieved by aggressively repairing mitral and/or tricuspid valves directly, which requires open-heart surgery (Bolling, et al.). The mitral valve annulus is reinforced internally by a variety of prosthetic rings (Duran Ring, Medtronic Inc) or bands (Cosgrove-Edwards Annuloplasty Band, Edwards Lifesciences Inc). The present paradigm of mitral valve reconstruction is therefore repair from inside the heart, with the annulus being buttressed or reinforced by the implantation of a prosthetic-band or ring. Since this is major open-heart surgery with intra-cavitary reconstruction, there is the attendant risk of complications and death associated with mitral valve surgery. Another approach has been to replace the mitral valve, which while addressing the problem, also requires open-heart surgery and involves implantation of a bulky artificial, prosthetic valve with all its consequences. Because every decision to perform major surgery requires some risk vs. benefit consideration, patients get referred for risky surgery only when they are significantly symptomatic or their mitral valve is leaking severely.

In contrast to the more invasive approaches discussed above, in specific instances of inferior left ventricular wall scarring causing mitral regurgitation, Levine and co-workers have suggested localized pressure or support of the bulging scar of the inferior wall of the heart from the outside.

Another less invasive approach to preventing global heart dilation is ventricular containment with a custom made polyester mesh, or cardiac support device (U.S. Pat. Nos. 6,077,218 and 6,123,662). These devices are designed to provide a passive constraint around both ventricles of the heart, and constrain diastolic expansion of the heart. Other devices include ventricular assist devices that provide cardiac assistance during systole and dynamic ventricular reduction devices that actively reduce the size of the heart. However, this technique does not specifically address valve leakage using a device that reinforces the base of the heart in all phases of the cardiac cycle.

Accordingly, there is a need to provide a less invasive, simple technique of repairing, reinforcing, reducing or stabilizing the base of the heart and its underlying valves (mitral and tricuspid valves) from the outside.

DISCLOSURE OF THE INVENTION

The present invention addresses the problems discussed above by providing a device for the treatment of certain heart disorders, in particular mitral and/or tricuspid valve insufficiency. The device aims to reduce the size of the base of the heart that contains these valvular structures. In addition, the present invention can be used to address progressive dilatation of any localized area of the heart, such as the atrial or ventricular myocardium, or the cardiac base. It does so by providing external re-enforcement or remodeling of the cardiac base. As used herein, the surgical procedure for implanting the device is referred to as ibasal annuloplasty of the cardia externally ("BACE") and the device is referred to as the external cardiac basal annuloplasty system ("ECBAS") or BASE System.

In one embodiment, a customized or specially constructed biocompatible strip is implanted along the base of the heart at the level of the atrio-ventricular groove. The strip or mesh is between 2 and 5 cms wide and is secured by 2 rows of clips or sutures, one on the atrial side and the other on the ventricular side of the atrio-ventricular groove. Specific care is taken to avoid injury to the circumflex and right coronary arteries and the coronary sinus. This procedure may be performed either as a stand-alone procedure or as an adjunct to other cardiac surgery. Additionally, it may be performed with or without the aid of cardio-pulmonary bypass.

Another embodiment of this approach is a device or strip, which once implanted at a certain size, can be tightened over time either by inflation of an attached chamber or programmed to return to a pre-formed size (based on elasticity or pre-existing memory) of the material used.

Another embodiment of this device, while externally stabilizing the base of the heart, also provides a localized increase in contraction along any segment of the base to improve contractile function. This may be accomplished by the aid of contractile metal or modified muscle or other cells.

Variations of the device include a complete stabilization of the base of the heart, or a partial stabilization around the expansile portions of the mitral and tricuspid valves by a biocompatible strip.

Another variation seeks to use ports along the device that will facilitate delivery of specialized drugs, gene therapeutic agents, growth factors, etc.

A specific variation incorporates the use of epicardial bi-ventricular pacing electrodes implanted along with the BACE-Sys, where multi-site pacing might be indicated.

The invention also provides a method of implantation, which may be through a conventional full median sternotomy with the strip being secured by sutures, or a minimally invasive approach whereby the device/strip may be implanted by a specialized implantation system using adhesives, self-firing clips, sutures, etc.

Another modification of this technique is the local application of prosthetic material to stabilize scars of the heart to prevent their expansion (local ventricular stabilization).

In an alternate embodiment, the device incorporates additional strips to be used in concert or as an extension to provide localized support to areas of ventricular reconstruction or areas of fresh infarction or old scar.

DESCRIPTION OF THE PREFERRED EMBODIMENTS

The present invention is directed to external support of the base of the heart. The support functions to decrease, and/or prevent increases in, the dimensions of the base, and in particular the atrio-ventricular junction, beyond a pre-determined size. The device is designed to reduce the size of the cardiac base in a manner similar to an internal annuloplasty band or ring.

This invention is particularly suited for use in regurgitation of the mitral and tricuspid valves. The device may also be used prophylactically in heart failure surgery to prevent further cardiac basal dilation or expansion even if the underlying mitral and tricuspid valves are competent. The device may be used in moderate or advanced heart failure to prevent progression of basal dilatation or reduce the size of the dilated base.

As used herein, "cardiac base" refers to the junction between the atrial and ventricular chambers of the heart, also known as the atrio-ventricular junction marked externally by the atrio-ventricular groove. This is easily identified in the change of appearance of the cardiac muscle and also the presence of arteries and veins.

The heart is enclosed within a double walled sac known as the pericardium. The inner layer of the pericardial sac is the visceral pericardium or epicardium. The outer layer of the pericardial sac is the parietal pericardium. The term "endocardial surface" refers to the inner walls of the heart. The term "epicardial surface" refers to the outer walls of the heart.

The mitral and tricuspid valves sit at the base of the heart and prevent blood from leaking back into the atria or collecting chambers. See FIG. 1. Mitral regurgitation is a condition whereby blood leaks back through the mitral valve into the left atrium. Over time, this creates a damming of blood in the lungs causing symptoms of shortness of breath. The left heart particularly the left ventricle has to pump a greater volume of blood as a result causing greater strain on this chamber.

Figure 2:
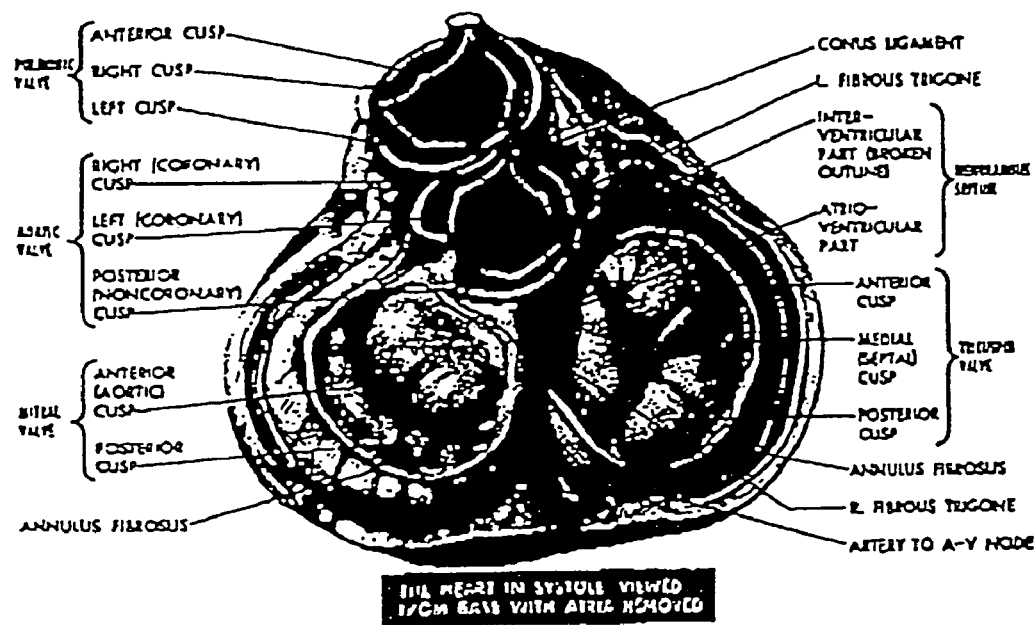
FIG. 2 depicts a cross-section of the base of the heart between the dotted lines depicted in FIG. 1.
Figure 3:
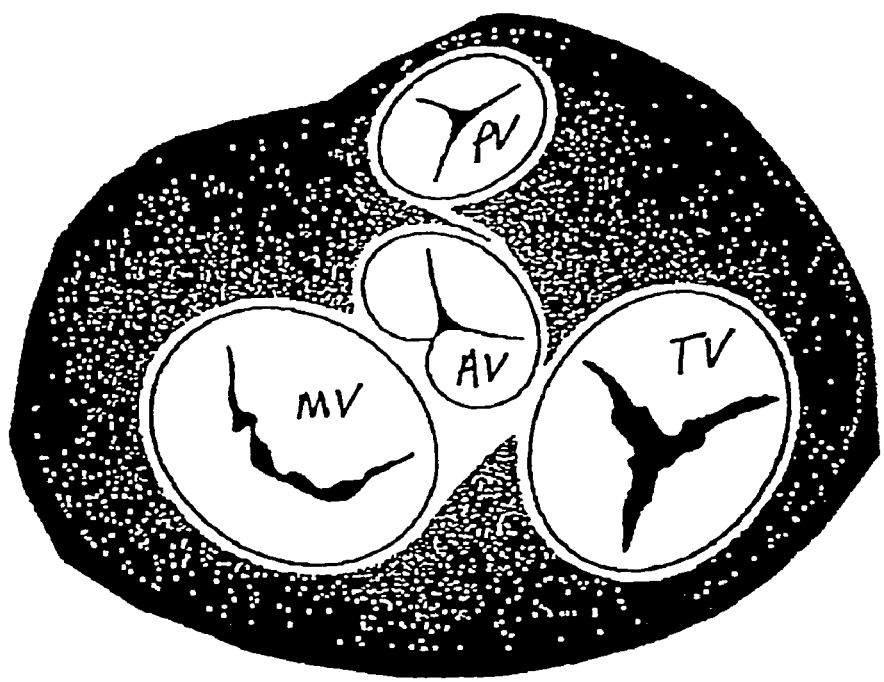
FIG. 3 depicts a cross-sectional schematic diagram of the base of the heart. As depicted therein, PV=pulmonary valve, MV=mitral valve, AV=aortic valve and TV=tricuspid valve.

Dilatation of the mitral annulus occurs maximally in the posterior portion of the annulus, which is not supported by the cardiac fibro-skeleton. FIG. 2 is an anatomic diagram of the base of the heart, showing the valves and the structures in contact with them. FIG. 3 is a schematic representation of the valves at the cardiac base.

Figure 4:
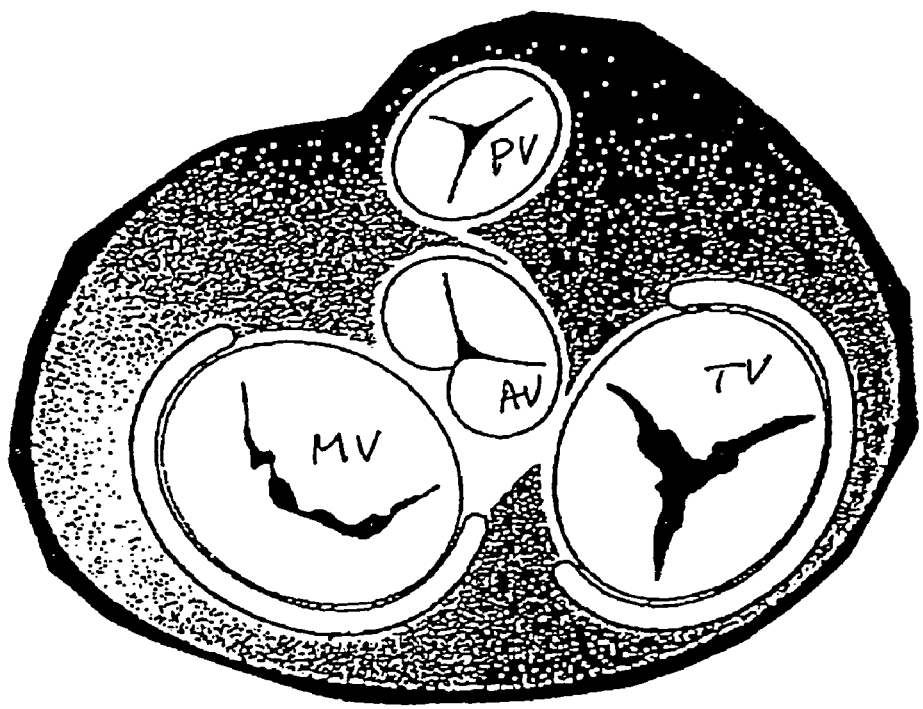
FIG. 4 depicts a traditional method of repairing MV and TV with bands inside the heart.

Mitral valve repair or replacement at present is always performed from inside the heart with the aid of cardiopulmonary bypass. Rings are implanted along the inner surfaces of the entire or expansile portions of the mitral and tricuspid annuli (FIG. 4). Alternatively, when mitral valve malfunction is severe, replacement of the valve with a prosthetic valve may be indicated.

Overview

Figure 5:
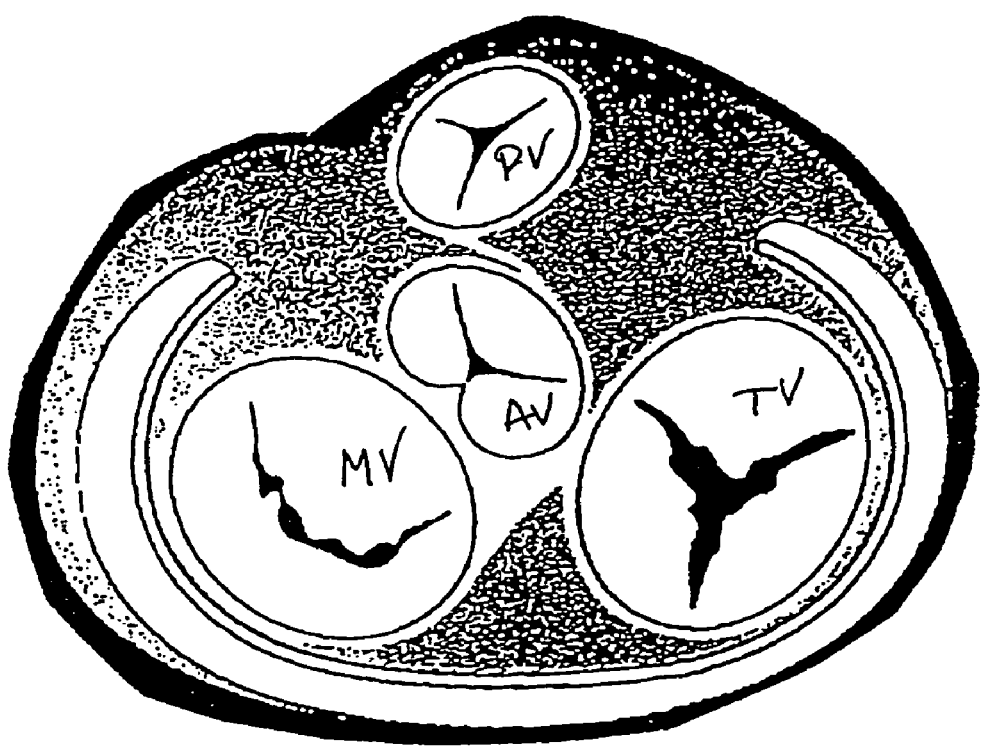
FIG. 5 depicts basal angioplasty of the cardia externally.

The basal ventricular stabilization of the present invention works by using a prosthetic material such as polyester mesh anchored or sutured to the base of the heart at the level of the atrio-ventricular groove. This serves to stabilize the mitral and tricuspid annuli from the outside (FIG. 5). This technique reduces the complexity of the procedure and minimizes the invasive nature and complications from work on the valve. This technique is of particular benefit in patients that have morphologically normal valves with annular dilatation. The device can be applied and anchored to the cardiac base, with the heart beating, without the aid of cardiopulmonary bypass.

Many patients with moderate degrees of mitral regurgitation are not treated surgically, because the risks of surgery outweigh the potential benefits in this group of patients. However, patients with conditions such as chronic heart failure tend to get very symptomatic even with moderate degrees of mitral regurgitation. These groups of patients would benefit from the less invasive procedures, which are the subject of the present invention. Thus, the potential of this technique in treating mitral regurgitation as a minimally invasive procedure has great appeal as the population ages and more patients manifest with symptoms of heart failure. It also can be applied en passant in patients undergoing coronary artery surgery without the aid of a heart-lung machine.

Device Parameters

The device of the present invention can be constructed of any suitable implantable material. Examples of such materials are well known in the art and include, e.g., synthetic polymers such as polyester, polytetrafluoroethylene, polypropylene, teflon felt, etc., as well as metallic materials such as stainless steel. Such metals may provide "memory", such that they return to a specific shape after deformation, and in this manner provide an element of dynamic contraction. In yet another embodiment, the device may be constructed either partially or completely by natural materials, such as polyglycolic acid or compressed and/or crosslinked collagen, which may or may not be reinforced with synthetic polymers or other means. Any material is suitable that is biocompatible, implantible, and preferably has a compliance that is lower than the heart wall. Other variations include incorporation of elastic material or elastin ingrowth into the biomaterial.

Figure 6:
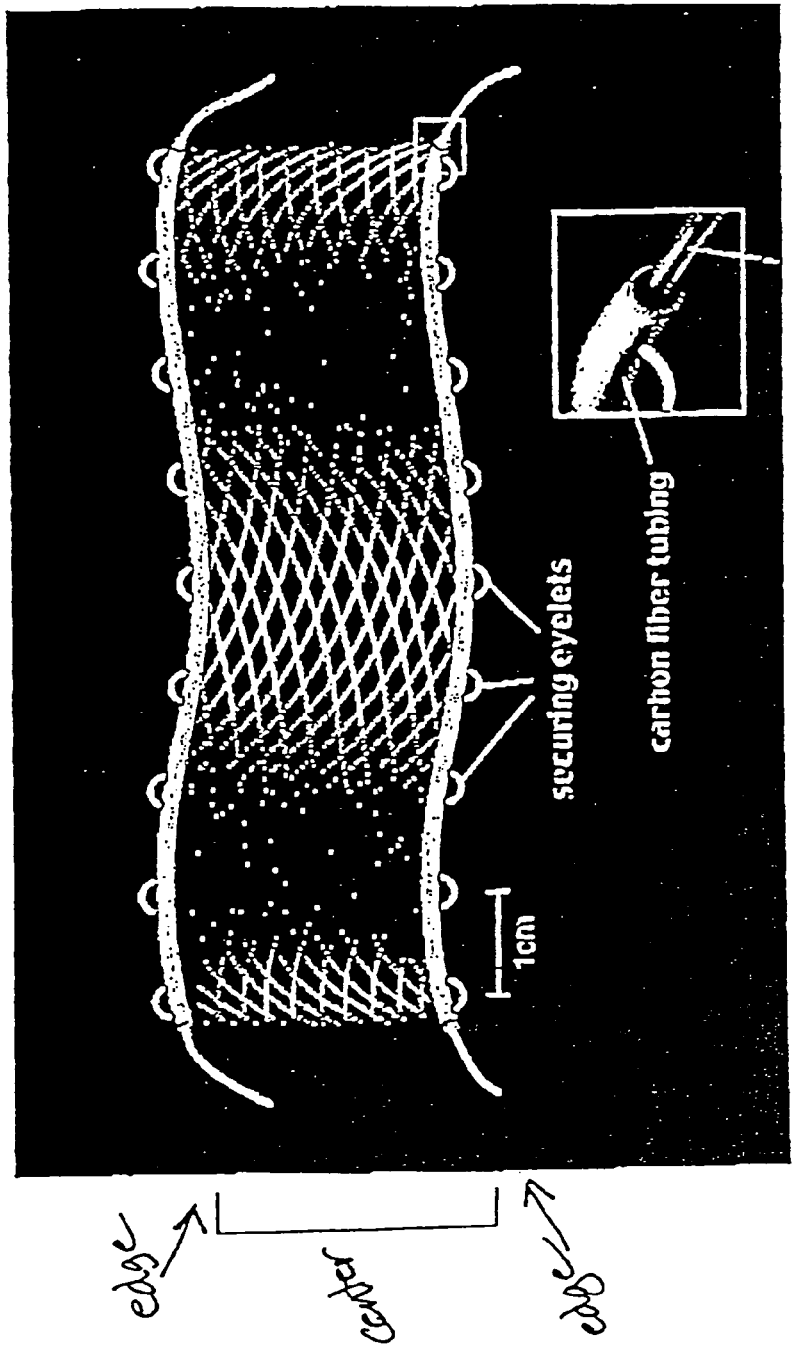
FIG. 6 depicts a representative embodiment of the device of the present invention.
Figure 7:
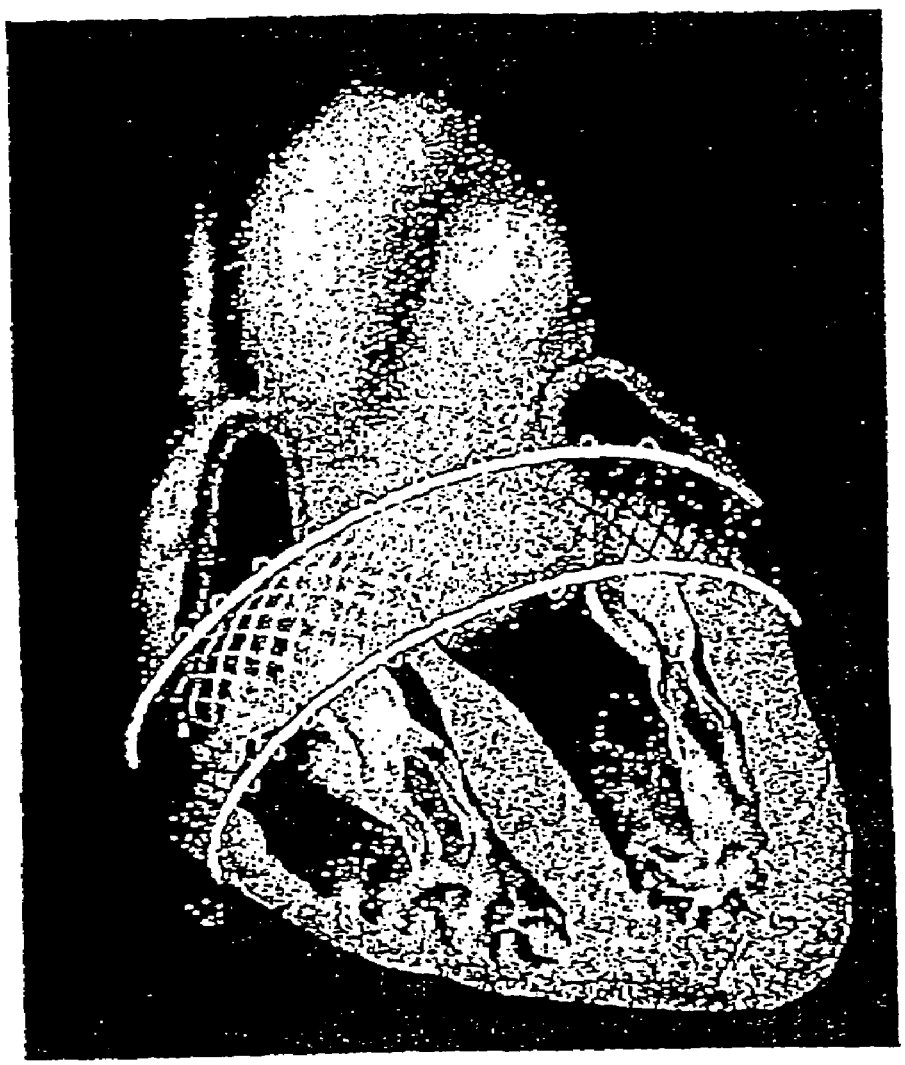
FIG. 7 depicts a schematic drawing of a heart with a representative device in place.

As shown in FIG. 6, the preferred device is in a "strip" configuration and comprised of two edge members and a center portion, each of which may be constructed by the same or different material. In one embodiment (not shown), there is no distinction between the edge members and the center portion and the device is completely uniform from top to bottom.

The center portion of the device may be in the form of a solid single or multi-layer sheet, but is preferably of an open mesh, porous or woven design, such that the exterior of the heart is not completely covered and therefore remains exposed to the surrounding tissue. The size of the openings in the mesh can vary, for example from 2 mm to 2 cm, and can take any shape, such as circular, square, octagonal, triangular, or irregular. In a preferred embodiment, the center portion of the device is a mesh as depicted in FIG. 6.

The center portion may also be adapted for the delivery of various therapeutic agents, such as growth factors or plasma proteins. In addition, it may be adapted to facilitate cellular growth, which in turn may facilitate anchorage of the device.

The device may be designed to completely circle the base of the heart, or it may be a "C" shape, in which case it is specifically designed and implanted so as to not impede blood flow through the aorta and pulmonary artery.

The biomaterial from which the device is constructed may also be radiolucent, radio-opaque or have radio-opaque markers at present intervals to monitor the movement of the cardiac base in real-time using fluoroscopy and to facilitate implantation.

The device may be completely rigid prior to implantation, or may have regions of varying rigidity. However, it is important that the device is sufficiently flexible to move with the expansion and contraction of the heart without impairing its function. It should, however, be designed to prevent expansion of the cardiac base during diastolic filling of the heart to a predetermined size. Since the size expansion parameters of a beating heart are well known, this can be accomplished by testing the device in vitro by applying forces that mimic heart expansion.

The edges of the device, which are depicted in FIG. 6 having securing eyelets attached thereto, may be constructed of a more rigid material, such as carbon fiber tubing. In addition, means of making the device, or portions thereof, such as one or both edges and/or the center portion, more or less rigid post-implantation are also within the present invention. For example, the center portion may be constructed of a partially biodegradable material and may become more flexible-after implantation when the biodegradable material is hydrolyzed by the surrounding tissues and fluids. Alternatively, the edges may be provided with means for making them more rigid or flaccid prior to implantation, such as by inflating/deflating closed chambers. Many alternate means for adjusting the rigidity/flexibility of the device, or portions thereof, would be easily adapted from other mechanisms known in the surgical arts.

Device Attachment

The device may be attached to the outside of the base of the heart by any known method. For example, attachment may be biological, chemical or mechanical. Biological attachment may be brought about by the interaction of the device with the surrounding tissues and cells, and can be promoted by providing appropriate enhancers of tissue growth. Alternatively, chemical attachment may be provided by supplying a mechanism for chemical attachment of the device, or portions thereof, to the external surface of the heart. In yet another embodiment, the rigidity and tightness of the device around the heart may provide for sufficient mechanical attachment due to the forces of the heart against the device without the need for other means of attachment. In a preferred embodiment, however, as depicted in FIG. 6, the device further comprises attachment members, such as the eyelets shown therein. Specific anchor points or loops made of any biocompatible and implantable material may be attached to the edges or to the center portion or both to facilitate anchoring. Suitable materials include, inter alia, polyester, polypropylene or complex polymers. Alternative attachment members may comprise suture materials, protrusions that serve as sites for suturing or stapling, as well as other structural members that facilitate attachment to the surface of the heart.

Device Size

Although the size of the device depends on the purpose for which it is being implanted, it is contemplated that the device will be wide enough (measured from the outside of the first or top edge, i.e. the base edge, to the outside of the second or bottom edge, i.e. the apex edge) to provide efficient support to the atrio-ventricular grove. Accordingly, in one embodiment, the device is between 2 and 5 centimeters wide. In other embodiments, the device may be adapted to provide support over a larger area of the heart. This would provide specifically for reinforcement of areas of scar or muscular weakness as in dyskinetic infracted areas of the myocardium.

Figure 1:
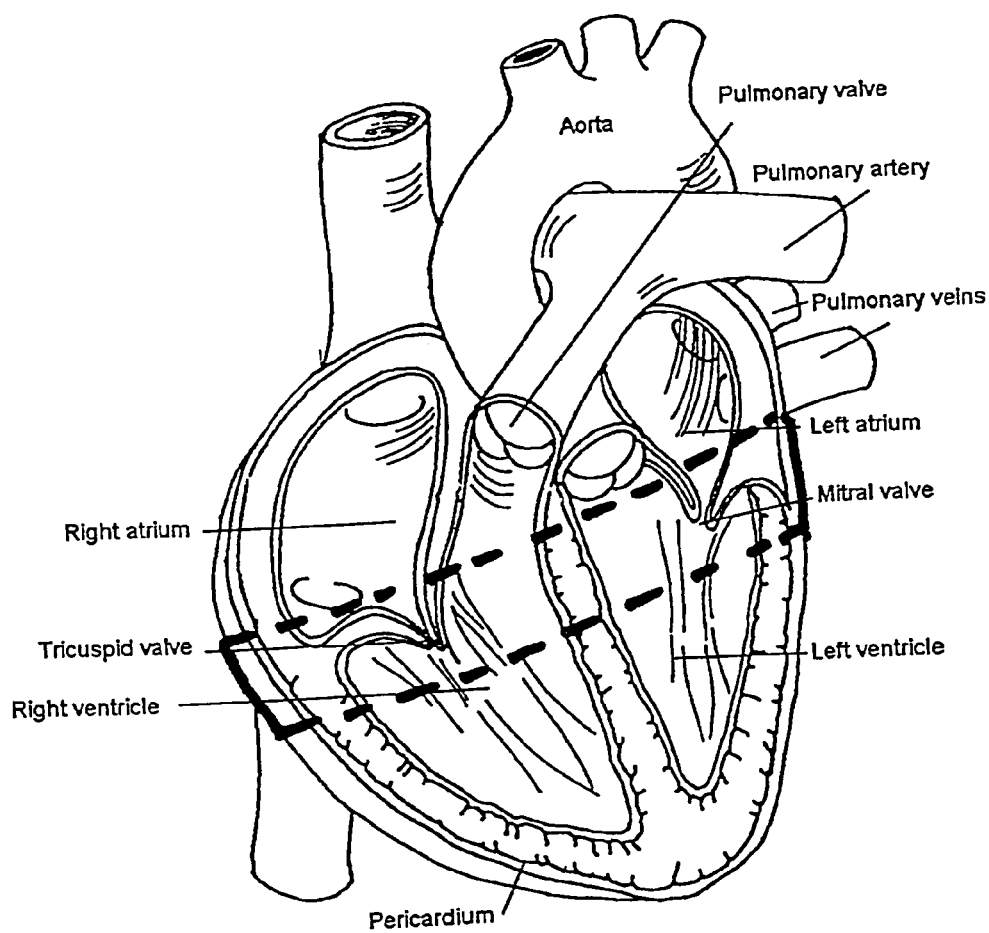
FIG. 1 depicts a cross-section of the heart, showing the approximate location of a representative embodiment of the device of the present invention by dashed lines.

As shown in FIG. 1, the distance between the base and the bottom of the apex of the heart can be expressed as distance "X". Because the focus of the device of the present invention is base stabilization, it is generally preferred that the width of the device be less than or equal to ½ X, and be adapted for placement around the top half of the distance X, i.e. closer to the base than the bottom of the apex.

Implantation

The ECBAS or BASE system may be implanted through a conventional midline total sternotomy, sub maximal sternotomy or partial upper or lower sternotomy. Alternatively, the device may be implanted through a thoracotomy incision, or a Video Assisted Thoracoscopic (VAT) approach using small incisions. The BASE system can also be implanted by a sub-costal incision as in the Sub-Costal Hand-Assisted Cardiac Surgery (SHACS). Additionally, he BASE system may be implanted with sutures onto epicardium or clips, staples, or adhesive material that can secure the device on the heart accurately. The device may also be implanted using robotic placement of the device along the posterior aspects of the base of the heart.

The method of implantation and the adequacy of the external annuloplasty can be dynamically assessed by intraoperative trans-esophageal echocardiography, epicardial echocardiography or trans-thoracic echocardiography. The size of the device is assessed based on external circumference measurements of the cardiac base in the fully loaded beating heart state.

Versions of the BACE Systems a. Complete Versus Partial BACE

The ECBAS may completely encircle the cardiac base or just partially support the mitral and tricuspid valve portion of the cardiac base.

b. BACE with Extension

In one embodiment, a limited extension of the ECBAS or a remote patch may be applied to reinforce an area of myocardium that has been reconstructed to exclude an aneurysm or scar.

c. BACE with Pace

In another embodiment, the ECBAS has attached close to or within it epicardial steroid eluting pacing wires that can facilitate multi-site ventricular pacing for heart failure.

d. Dynamic BACE

In this embodiment, the device has fluid filled chambers that may be inflated gradually over time, to gradually reduce the size of the cardiac base. These chambers may also effect passive transfer of energy to facilitate diastolic and systolic support with a closed pericardium e. Smart & Dynamic BACE In this embodiment, the bio-material would have the capability to shrink to a pre-formed size over a period of time, based on the memory of the material or some other programmable characteristic. This would achieve controlled reduction over a period of time of the base of the heart.

f. Cellular BACE

In this embodiment, the bio-material uses available matrix technology, and seeding of appropriate cells to provide dynamic reduction and assistance to the cardiac base.

References:

1. Pai R G, Silvet H, Amin J, Padmanabhan S: Prognostic importance of mitral regurgitation at all levels of LV systolic function: Results from a cohort of 8931 patients. Circulation 2000;102(18) Suppl. II: 369.

2. Bolling S F, Pagani F D, Deeb G M, Bach D S: Intermediate-term outcome of mitral reconstruction in cardiomyopathy. J Thorac Cardiovasc Surg 1998;115:381-8.

3. Timek T A, Dagum P, Lai D T, Liang D H, Daughters G T, Ingels N B, Miller D C: Pathogenesis of mitral regurgitation in tachycardia induced cardiomyopathy (TIC). Circulation 2000;102(18) Suppl. II:420.

4. Liel-Cohen N, Guerrero J L, Otsuji Y, Handschumacher M, Rudski L, Hunziker P R, Tanabe H, Scherrer-Crosbie M, Sullivan S, Levine R A: Design of a new surgical approach for ventricular remodeling to relieve ischemic mitral regurgitation: insights from 3-dimensional echocardiography. Circulation2000; 101(23):2756-63.

5. Lamas G A, et al: Poor survival in patients with mild to moderate mitral regurgitation. Circulation 1997;96:827.

EXAMPLES

Example 1

BACE Procedure

Abstract: Over a 12 month period, ten patients underwent Basal Annuloplasty of the Cardia Externally (BACE), to correct moderate mitral regurgitation. This technique involves securing a specially constructed polyester mesh like device to the epicardial surface of the cardiac base, at the level of the atrio-ventricular groove. These procedures were performed in conjunction with coronary artery surgery in all patients. All patients demonstrated a dramatic improvement in functional status, quality of life, mitral regurgitation and function of the heart. BACE can be performed safely with expectation of a good clinical outcome as an adjunct to conventional heart surgery.

Clinical Approach and Experience:

Careful pre-operative screening included radionuclide ventriculography to document left ventricular ejection fraction, a detailed trans-thoracic echocardiogram, a coronary angiogram, and in most cases a stress thallium and/or a Positron Emission Tomographic Scan looking for myocardial viability. The functional status of the patients were carefully documented by a heart failure cardiologist and nurse.

Ten patients who were undergoing conventional cardiac surgery, usually in the setting of poor cardiac function with moderate mitral regurgitation, were enrolled. All of these patients had coronary artery bypass surgery. All of them had at least moderate mitral regurgitation pre-operatively and intra-operatively (confirmed by trans-esophageal echocardiography). All of these patients had the Basal Annuloplasty of the Cardia Externally (BACE) performed with a polyester mesh constructed intra-operatively, based on the measured circumference of the cardiac base.

Surgical Technique:

The circumference of the base of the heart at the level of the atrio-ventricular groove was measured before the patient was connected to cardio-pulmonary bypass (CPB). Based on these measurements, a strip of polyester mesh measuring 2.5 to 3 cm in width was cut to size and fashioned, such that its length would be less than the basal circumference by about 2.5 to 4.5 cms. Once the patient was connected to cardiopulmonary bypass, the coronary artery bypass grafts were performed. Left ventricular reconstruction was performed when indicated.

The constructed BACE mesh was anchored posteriorly at the level of the atrio-ventricular groove, on atrial and ventricular sides with combination of 4/0 Ticron™ sutures and hernia staples, which were placed about 1.5 to 2 cm apart. The mesh was secured laterally as well. Final assessment of the tension and the securing of the BACE system was performed with the patient weaned off cardio-pulmonary bypass with the heart filled to pre CPB levels. The mesh was then tightened and secured just as the mitral regurgitation was abolished on trans-esophageal echocardiographic monitoring.

Post-Operative Course:

All these patients had trivial to mild mitral regurgitation at the completion of the procedure. At follow-up, 3, 6 and 12 months post-operatively, all of these patients demonstrated improved cardiac function (as measured by left ventricular ejection fraction), improved functional status and quality of life, and were able to maintain their improvement in the degree of mitral regurgitation. Radionuclide ventriculography was used to determine the left ventricular ejection fraction pre- and post-operatively. Compared to a preoperative value of $25\pm3.1\%$ (n=8), the ejection fractions improved to $40\pm14.2\%$ and $39.3\pm5.7\%$ after 3 and 6 months post-operatively, respectively ($p<5$). Likewise, the New York Heart Association (NYRA) classification was used as an index of functional heart status. Compared to a pre-operative value of $3.11\pm0.33$ (n=8), the NYHA improved to $1.17\pm0.41$ after 3 months post-operatively ($p<5$). Mitral regurgitation (graded 1 to 4) was also observed to improve dramatically from 3.01 pre-operatively to 0.1 post-operatively after 6 months ($p<5$). In addition, there was improvement in tricuspid regurgitation as well.

Discussion: Dilatation of the cardiac base often accompanies heart failure. This may be a secondary development due to volume overload and increased left ventricular wall stress. In cases of mitral or tricuspid valvular heart disease, annular dilatation occurs along with decompensation of the regurgitant lesions. Severe annular dilatation accompanies severe regurgitation. However, significant basal dilatation may co-exist with moderate or moderately severe atrioventricular valve regurgitation. Since repair of these conditions requires intra-cavitary repair of the affected annulus, the majority of surgeons tend to leave moderate and moderately severe mitral and/or tricuspid regurgitation alone. Using the methods and apparatuses of the present invention, these conditions can be corrected from the outside of the heart. Furthermore, the correction can be tailored under trans-esophageal echocardiographic guidance. This avoids intra-cavitary manipulation. In selected cases, this procedure could be performed with heart beating also and without using the heart-lung machine, making it an "off-pump" procedure.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in hematology, surgical science, transfusion medicine, transplantation, or any related fields are intended to be within the scope of the following claims.

Example 2

Comparative and Long Range Studies Using BACE Procedure

Twelve patients were treated with the BACE procedure as described in Example 1. All of the patients had pre- and post-operative studies at 3, 6, 12 and 18 months, including echocardiography and radionuclide ventriculography to look at cardiac function, amount of mitral regurgitation and the size of the hearts. All twelve patients were very symptomatic, with the majority in New York Heart Association (NYHA) class III status. The mean left ventricular ejection fraction (LVEF) was 25% preoperatively and all patients had moderate mitral regurgitation.

The BACE procedure was performed on cardio-pulmonary bypass with the heart decompressed. The procedure took approximately 15 minutes of extra bypass time and about 5 minutes of extra cross-clamp time.

The results are shown below in Table 1. As shown, the BACE procedure dramatically improved cardiac function and was at least equivalent to mitral valve repair eighteen months post-operatively.

TABLE 1

| | BACE Procedure Results | | | |
|---|---|---|---|---|
| | Pre-Op | 6 months | 12 months | 18 months |
| NYHA Functional Status | 3.11 | 1.14 | 1.2 | — |
| Left Ventricular Ejection Fraction (%) | 25.0 | 39.3 | 43.1 | 44.5 |
| Degree of Mitral Regurgitation - BACE Patients | 2.8 | — | — | .3 |
| Degree of Mitral Regurgitation - Mitral Valve Replacement Patients | 3.7 | — | — | .7 |

What is claimed is:

1. A device for use as an external stabilizer of a heart base comprising a strip of biocompatible, implantable material comprising a top edge and a bottom edge having a width therebetween, wherein the width is about 2 to 5 cms, and wherein the device prevents basal dilation during all cardiac phases.

2. The device of claim 1, further comprising a center portion.

3. The device of claim 2, wherein the center portion further comprises an open mesh.

4. The device of claim 3, wherein the open mesh further comprises opening sizes between 2 mm to 2 cm, when measured along the longest axis.

5. The device of claim 2, wherein the top and bottom edge further comprise a metal.

6. The device of claim 2, wherein the center portion further comprises a polyester mesh.

7. The device of claim 2, further comprising attachment members.

8. The device of claim 7, wherein the attachment members further comprise eyelets.

9. A method for treating heart disorders comprising epicardially placing a device according to claim 1 around the base of the heart.

10. The method according to claim 9, further comprising placing the device in the atrio-ventricular groove.

* * * * *